United States Patent [19]

Khromov-Borisov et al.

[11] 4,060,652

[45] Nov. 29, 1977

[54] NONDEPOLARIZING MUSCLE RELAXANT

[76] Inventors: Nikolai Vasilievich Khromov-Borisov, ulitsa Nalichnaya, 36, korpus 9, kv. 214; Samuil Fedorovich Torf, ulitsa Kurchatova, 4, kv. 86; Valentina Pavlovna Cherepanova, Vasilievsky Ostrov, 4 linia, 19, kv. 5; Anatoly Fedorovich Danilov, Vasilievsky Ostrov, 9 linia, 54, kv. 36; Larisa Alexandrovna Starshinova, Annikov prospekt, 13, kv. 64, all of Leningrad, U.S.S.R.

[21] Appl. No.: 689,978

[22] Filed: May 26, 1976

[51] Int. Cl.$^2$ .............................................. A61K 31/14
[52] U.S. Cl. ............................ 424/329; 260/567.6 P
[58] Field of Search .................. 424/329; 260/567.6 P

[56] References Cited

U.S. PATENT DOCUMENTS 2,520,275  8/1950  DuBois et al. ................ 260/567.6 P
3,929,886  12/1975  Isard ............................. 260/567.6 P

FOREIGN PATENT DOCUMENTS 741,112  11/1955  United Kingdom ............. 260/567.6

*Primary Examiner*—Stanley J. Friedman

[57] ABSTRACT

A nondepolarizing muscle relaxant containing, as active principle ingredient, p,p"-bis-triethylammonio-n-terphenyl dibenzenesulphonate in a pharmaceutical carrier is described. The proposed preparation is used as a 0.5 per cent aqueous solution.

Said muscle relaxant possesses high potency and selectivity. When given in a myoparalytic dose, it does not affect the arterial pressure. The preparation is nontoxic, its effect is quickly and fully removed by cholinesterase inhibitors, which ensures higher safety and better control of muscle relaxation compared with the action of the known muscle relaxants α-tubocurarin and pancuronium.

5 Claims, No Drawings

NONDEPOLARIZING MUSCLE RELAXANT

This invention relates to medicinal and curare-like preparations, and more particularly it relates to nondepolarizing muscle relaxants. Nondepolarizing muscle relaxants are used to block nervomuscular conduction of skeletal muscles in surgical operations, in treating tetanus, and in some endoscopic examinations.

Muscle relaxants were first used in surgical operations in 1942 at the suggestion of Griffiths. At the present time, muscle relaxants are used in all operations requiring anesthesia. Depending on the block mechanism, all muscle relaxants, are divided into two groups: depolarizing and nondepolarizing relaxants.

At present, only the dicholine ester of succinic acid, known also as dithilin, myorelaxin, listenon, or succinylcholine, is used as a depolarizing skeletal muscle relaxant, while other preparations in this group, viz., decamethonium and imbretil, are no longer used mostly due to the absence of means by which the action of these preparations could be discontinued.

The wide use of succinylcholine is explained by the quickness and short duration of its effect, which is especially important in cases where short relaxation of muscles is required. But in patients with hepatic dysfunction and low cholinesterase content of plasma, the action of a common dose of the preparation can last for a period of a few hours.

Whenever it is necessary to induce prolonged relaxation with succinylcholine, it is given in periodic injections or with drop instillation. However, paralysis of skeletal muscles and apnea (the transient cessation of respiration, the absence of active respiration) can develop in patients with normal cholinesterase level. Since depolarizing muscle relaxants do not have sufficiently effective antagonists, serious difficulties can arise in controlling these complications. Moreover, the action of succinylcholine is associated with development of muscular pains. Increased content of potassium in blood, induced by depolarizing muscle relaxants (including succinylcholine) can produce grave complications in patients with cardivascular insufficiency. Furthermore, succinylcholine would usually raise arterial pressure and induce tachycardia. In rare cases, on the contrary, bradycardia and hypotension can develop, which become especially manifest when the preparation is given in combination with cyclopropane, fluorothane, and digitalis. The repeated administration of succinylcholine is fraught with the danger of possible disorders in the cardiac rhythm, and even complete cessation of the heart activity. This is especially true in the case of patients with heart diseases, as well as with disordered potassium metabolism. In view of these disadvantages inherent in succinylcholine and other depolarizing muscle relaxants, anesthesiologists have arrived at the conclusion that nondepolarizing muscle relaxants should preferably be used.

α-Tubocurarin (Burroughs Wellcome Co, London) and pyrolaxon (gallamine, flaxedil), belonging to the group of nondepolarizing relaxants, have been widely used for many years. These preparations, however, also have disadvantages; α-tubocurarin given in a myoparalitic dose produces histamine from tissues and blocks sympathetic ganglia and, hence, lowers the arterial pressure. Pyrolaxon blocks parasympathetic ganglia and produces tachycardia.

Nondepolarizing muscle relaxant pancuronium (pavulon, Organon Inc. W. Orange, N.Y. 07052) which is a bis-quarternary aminosteroid has been popular in recent years. It is 5 to 10 times more active than α-tubocurarin with respect to the nervomusclar blocking action and 2.5 times less active with respect to blocking conduction in sympathetic ganglia. The myoparalytic action lasts for the same period of time as that of α-tubocurarin. Pancuronium does not induce production of histamine from tissues, nor does it lower arterial pressure. Its myoparalytic action can be removed with proserpin, and cases with difficult decurarization occur less frequently than with α-tubocurarin. Since this preparation does not reduce blood pressure, it can be given in greater doses. For example, on administration of pancuronium in a dose of 0.15 mg/kg body weight, favourable conditions for tracheal intubation are provided. In other words, pancuronium is devoid of the disadvantages inherent in α-tubocurarin and pyrolaxon, and is justly considered as the best nondepolarizing muscle relaxant.

But pancuronium has disadvantages of its own, too. Given in a myoparalytic dose, pancuronium often accelerates the pulse rate and increases arterial pressure. This, in turn, intensifies hemorrhage in operations.

The object of this invention is to provide a new nondepolarizing muscle relaxant that will be free of the disadvantages inherent in α-tubocurarin, pyrolaxon or pancuronium, completely safe in clinical use posses in addition, high selectivity and specificity of its action without affecting the other physiological systems and, finally, provide for safe and controlled muscle relaxation.

This object is attained in a new nondepolarizing muscle relaxant which, according to the invention, contains as the active principle p, p''-bis-triethylammonio-p-terphenyl dibenzenesulphonate and a pharmaceutical carrier.

The carrier for said active principle is water. The proposed relaxant can be used as a 0.5 per cent aqueous solution. The content of the active principle per intravenous injection is 5 mg/ml. The preparation contains a stabilizing agent, hydrochloric acid. The content of hydrochloric acid is 0.01 mg/ml for an intravenous injection.

Said muscle relaxant will hereinbelow be referred to as Tercuronium.

Tercuronium is a nondepolarizing muscle relaxant possessing activity and selectivity and has several advantages over the known nondepolarizing muscle relaxants α-tubocurarin and pancuronium. The advantages of the proposed new preparation will become subsequently clear from the following pharmacological description of Tercuronium.

Neuromuscular Blocking (curare-like) Action of Tercuronium

The preparation was studied in acute experiments on cats, rabbits, mice and pigeons, in experiments on phrenico-diaphragm preparations of rats, and also on the straight muscle of a frog abdomen. The properties of Tercuronium were compared with those of α-tubocurarin and pancuronium.

Experiments on Cats

Cats were narcotized (with chloralose, 50 mg per kg body weight, and urethane, 500 mg/kg, intraperitoneally) or decerebrated at the quadrigeminal bodies level.

The lungs were ventilated artificially whenever necessary. Contractions of the anterior tibial muscle were recorded in isotonic concitions in response to electric stimulation of the peripheral part of n. peroneus with supramaximum pulses of 0.1 msec at a frequency of 0.1–100 Hz.

With indirect stimulation of the muscle at a frequency of 0.1 Hz, the nervomuscular conduction was blocked (95–100 percent) in 40-60 seconds following an intravenous injection of Tercuronium in a dose ocf 0.08 ± 0.002 micromole per kg.

The block effect was at its maximum in 2 to 2.5 minutes and persisted for 2 to 4 minutes (ten experiments). The muscle contractility was completely restored in 10 ± 1.5 minutes after the Tercuronium injection. The dose of α-tubocurarin required to attain the same effect in the same conditions was 0.5 ± 0.03 micromole per kg (five experiments). For pancuronium, this does was 0.04 ± 0.001 mcM/kg.

The mean duration of Tercuronium effect is eight minutes, of pancuronium, nine minutes, and of α-tubocurarin, ten minutes. As Tercuronium is administered again, its blocking effect increases (as well as of α-tubocurarin and pancuronium) by 60 to 80 percent.

The blocking effect of Tercuronium is due to its action on the postsynaptic membrane of skeletal muscle. Thus, contraction of muscles induced by acetylcholine injected by the close intra-arterial method, was inhibited simultaneously with the block of the nervomuscular condution. While the muscle did not respond (in the period of complete inhibition) to indirect stimulation, it contracted in response to direct stimuli.

The action of Tercuronium was lessened by the action of neostigmin, succinylcholine, decamethonium, and acetylcholine and strengthened by α-tubocurarin. The blocking effect of Tercuronium is more manifest with increasing frequency of pulse stimuli. In cases with incomplete block of conduction of rare single pulses (0.1 Hz), tetanization of the motor nerve at a frequency of 50 to 100 Hz produces a pessimal reaction in the muscle. In the post-tetanic period, the contractile activity of the muscle, in response to direct stimulation with rare single pulses, is restored.

The blocking effect of Tercuronium is fully and immediately restored by intravenous injection of neostigmin given in a dose of 0.05 to 0.1 mg/kg. Antagonism of neostigmin toward tercuronium is stronger that toward α-tubocurarin or pancuronium. For example, even with a 5-fold dose of tercuronium, muscle contractility was restored already in 2 to 5 minutes following a single injection of neostigmin in a dose of 0.1 mg/kg, and in 15–20 minutes the recovery of the contactile function was complete.

In the case of pancuronium and α-tubocurarin, the restoration within these short periods of time could only be attained with 2–3 fold doses of these muscle relaxants. If the dose of pancuronium was increased 4 to 5 times, weak contractions of the muscle were observed not sooner than in 9 to 10 minutes and the contraction was, restored completely only 30 minutes after the injection of neostigmin (six experiments). The restoration of muscle contractility is delayed even longer in the case of α-tubocurarin. In experiments with a 4-fold dose of d-tubocurarin, weak contractions of the muscle could only be observed in 20 to 25 minutes and the muscle function was restored completely in 40 to 70 minutes (three experiments), and neostigmin proved of low efficacy with a five-fold dose of α-tuborurarin (three experiments).

Experiments on Rabbits

In experiments (a total of twenty) on non-narcotized rabbits, the head-drop dose (HDD) was 0.022 ± 0.009 micromole/kg A complete blocking effect developed 1.5 to 2 minutes after administration of Tercuronium and persisted for 3 to 5 minutes. A few minutes later, the animal behaviour normalized. The same effect was attained with 0.18 ± 0.02 micromole/kg of α-tubocurarin (6 experiments) and 0.018 ± 0.001 mcM/kg of pancuronium (6 experiments). The time of onset and the duration of the blocking effect with all the three preparations were the same. Thus, the blocking effect of Tercuronium is somewhat lower than that of pancuronium and eight times more effective than that of α-tubocurarin.

In another series of experiments, we determined the intravenous dose of the muscle relaxants that caused death of 50% of the animals due to paralysis of the respiratory muscles — lethal dose 50% ($LD_{50}$). The $LD_{50}$ of Tercuronium is 0.03 mcM/kg, that of α-tubocurarin is 0.25 mcM/kg and that of pancuronium is 0.026 mcM/kg. The range of the muscle-relaxing action, expressed by the $LD_{50}$ to HDD ratio was 1.4 with all the three preparations.

In experiments on narcotized rabbits (chloralose, 50 mg/kg, and urethane, 500 mg/kg, given intravenously) the intravenous dose of Tercuronium that produced complete block of the ischio-gastrocnemius conduction was 0.025 ± 0.005 mcM/kg (five experiments). Neostigmin given in a dose of 0.1 mg/kg, during the period of complete block, always resulted in immediate and full restoration of the muscle contraction.

Experiments on Mice

In experiments on albino mice, the dose of Tercuronium injected into the tail vein, that inhibited the symptom of turning from the lateral position in 50 percent of mice ($ED_{50}$) was 0.06 mcM/kg (18 experiments); and 50 percent of mice perished from paralysis of the respiratory muscles ($LD_{50}$) following an injection of 0.09 mcM/kg of Tercuronium. The width of the muscle relaxing action of Tercuronium ($LD_{50}/ED_{50}$) was 1.5.

The $ED_{50}$ and $LD_{50}$ of pancuronium is 0.042 mcM/kg and 0.062 mcM/kg respectively, and the width of the muscle relaxing action is 1.5. The $ED_{50}$ and $LD_{50}$ of α-tubocurarin, according to literature, is 0.17 mcM/kg and 0.24 mcM/kg, respectively. Hence $LD_{50}/ED_{50}$ is 1.4.

Thus, the myoparalytic action of Tercuronium in experiments on mice is several times lower than that of pancuronium and several times higher than that of α-tubocurarin.

Experiments on Pigeons

On intravenous injection of Tercuronium in a dose of 0.2 mcM/kg ($ED_{50}$) to pigeons, weak paralysis developed that persisted 2.5 to 3 minutes. Thus, in experiments on pigeons, Tercuronium shows the nondepolarizing effect as well.

In experiments on phrenico-diaphragm preparations of rats, isolated by the Bulbring method, the block of the nervomuscular conduction developed under the action of Tercuronium in a concentration of $2 \times 10^{-6}$ m/litre.

In experiments on isolated straight muscles of the frog abdomen (Rana tempraria) the concentration of Tercuronium, that weakened the action acetylcholine, was $2.0 \pm 0.04 \times \times 10^{-7}$ m/l. Tercuronium did not produce contractions in the muscle.

Inhibition of Respiration

In experiments on narcotized and decerebrated cats, respiration was inhibited and stopped by a curare-like paralysis of the diaphragm produced by Tercuronium. This developed simultaneously with the block of the nervomuscular conduction in the anterior tibial muscle. The respiration was restored simultaneously with the restoration of the muscle contraction. The same effect was observed with α-tubocurarin and pancuronium. In conditions of artificial ventilation of the lungs, bronchospasm did not develop even with 200–1000-fold dose of Tercuronium. The same result was obtained in experiments on rabbits. The ratio of $LD_{50}$ in experiments on rabbits and mice, as specified above, also provides data on the that Tercuronium produces on respiration. Since the $LD_{50}$ to $ED_{50}$ ratio does not substantially differ with Tercuronium, pancuronium and α-tubocurarin, the blocking doses of these muscle relaxants equally inhibit respiration.

Effect of Tercuronium on Arterial Pressure

Experiments were carried out on narcotized cats and rabbits (50 mg/kg of chloralose and 500 mg/kg urethane, intraperitoneally) and also on cats decerebrated at the quadrigeminal level. The blood pressure in the carotid artery was recorded with a mercury pressure gauge. The preparations were injected intravenously.

In conditions of active ventilation of the lungs, administration of Tercuronium, α-tubocurarin or pacuronium in doses that inhibit respiration, produced asphyxial rise in the arterial pressure.

In conditions of artificial ventilation of lungs, on administration of Tercuronium in a dose producing complete block of the nervomuscular conduction, the arterial pressure was not affected. When Tercuronium was given in a quantity ten times exceeding the myoparalytic dose (0.8 mcM/kg) an insignificant and transient reduction (10 to 20 mm Hg) of the blood pressure was observed. The animals (7 cats and 5 rabbits) tolerated injections of very large doses of Tercuronium, viz., 10–20 mcM/kg, which is 200 times higher than the myoparalytic dose. The blood pressure in this case quickly and sharply dropped and then slowly normalized. In all experiments, in 1 to 2 hours, the arterial pressure restored completely or was close to the initial level.

On an injection of a myoparalytic dose of pancuronium the arterial pressure did not drop either. As the dose of pancuronium was increased 3 to 5 times, the arterial pressure rise (20 to 40 mm Hg) was stable. The effect produced by a 20-fold dose of pancuronium was moderately depressive.

A myoparalytic dose of α-tubocurarin always produced a marked but transient reduction in the arterial pressure. A 5-fold dose of α-tubocurarin produced a very marked depressive effect and the animals perished immediately. In some cases, the effect persisted for 2 to 3 hours of observation.

Thus, Tercuronium produces the mildest effect on the arterial pressure compared with the other two muscle relaxants.

Effect on Vegetative Nervous System

1. Effect on Sympathetic Ganglia

Experiments were carried out on narcotized cats. A peripheral part of the sympathetic column on the neck was stimulated with electric pulses at 5 Hz. The duration of the stimulus was 1 msec, the amplitude 5 V. The contractions of the third eyelid (nictiating membrane) and the arterial (carotid) pressure were recorded with a mercury pressure gauge. We determined the intravenous dose of Tercuronium, α-tubocurarin and pancuronium that decreased the height of contraction of the third eyelid by 50 to 60 percent in conditions of prolonged stimulation of the sympathetic column.

The ganglioblocking effect developed after injection of 0.8 to 1.0 mcM/kg of Tercuronium which 10 to 15 times exceeds the myoparalytic dose. Simultaneously with the relaxation of the third eyelid, the arterial pressure dropped as well. The maximum effect persisted for 2 to 3 minutes and then the contractions of the third eyelid and arterial pressure began to restore. In 8 to 10 minutes after administration of Tercuronium the third eyelid contractions and the blood pressure were completely normalized.

The same reduction of the height of the third eyelid contractions was observed with injection of 0.8 to 1.0 mcM/kg of α-tubocurarin which is only 1.5 to 2 times higher than its myoparalytic dose. The fall in the blood pressure was more distinct (compared with the effect produced by Tercuronium).

The ganglioblocking dose of pancuronium was 1.2 to 1.6 mcM/kg, which 30 times exceeds the myoparalytic dose.

Effect on M-cholinoreceptors and Conduction in Parasympathetic Ganglia

Experiments were carried out on narcotized cats (chloralose and urethane, intraperitoneally).

In experiments on five animals, the left nervus vagus was cut. Platinum electrodes were placed on the peripherial part to stimulate the nerve with pulses of 0.1 msec and an amplitude of 5 V. The nerve was stimulated every 10 seconds at a frequency of 30 Hz. The pulse rate was recorded (ECG) and the blood pressure in the femoral artery was measured with a mercury pressure gauge.

The heart contractility was not affected by intravenous injection of 0.1 and 1.0 mcM/kg of Tercuronium in conditions without stimulation of n. vagus.

During period of stimulation of n. vagus, bradycardia developed and the arterial pressure dropped. On administration of 0.1 mcM/kg and 1.0 mcM/kg of Tercuronium the response of n. vagus to stimulation did not change.

In experiments on three narcotized cats, 0.1 to 1.0 mcM/kg of Tercuronium did not produce depression after intravenous injection of 3 mg/kg of acetylcholine.

Thus, Tercuronium given in a quantity 20 times exceeding its myoparalytic dose, does not produce any effect on the parasympathetic part of the vegetative nerve system. This is also proved by the results of other experiments on animals during which no bronchospasm or salivation were observed on the administration of a very large dose of Tercuronium.

Effect of Narcotics on Tercuronium Action

The action of ether, fluorothane, and sodium thiopental (given in narcotic concentrations) on the nervomuscular blocking activity and depressive effect (action on the arterial pressure) of Tercuronium, as well as on the neostigmin-Tercuronium antagonism was studied on decerebrated cats.

On the administration of 10 mg/kg of sodium thiopental the curare-like activity and the action of Tercuronium on the blood pressure did not change.

In condition of a deep ether-induced narcosis, the myoparalytic effect of Tercuronium, and also of α-tubocurarin and pancuronium, was intensified on an average of 20 to 30 percent. The action of Tercuronium on the arterial pressure did not substantially change in this case.

In conditions of a deep fluorothane-induced anesthesia, the myoparalytic effect of Tercuronium was intensified insignificantly, while the depressive effect failed to increase.

The neostigmin antagonism with Tercuronium action persisted against the back ground of narcotics.

Thus, Tercuronium is quite compatible with anesthetic agents such as ether, fluorothane, and sodium thiopental. The antagonistic action of neostigmin is fully preserved in such cases.

Study of 'Chronic' Toxicity of Tercuronium

Tercuronium was given intravenously to four rabbits, once a day in the course of twelve days, in a dose that induced the head-drop symptom, i.e. 0.02 to 0.024 mcM/kg. Physiological solution was injected instead of Tercuronium to two other rabbits (controls). The animals were weighed daily, their rectal temperature taken, and behaviour observed. Clinical analysis of urine and blood was performed three times. At the end of the experiment, the rabbits were killed (phlebotomy). The liver, kidneys, heart, lungs, adrenal glands, spleen, as well as marginal ear vein, into which Tercuronium had been injected, were histologically studied.

The sensitivity of the animals to Tercuronium did not change in the course of the experiment. The animal behaviour, and rectal temperature had no appreciable changes. We did not find any pathological inclusions or changes in the blood and urine analysis. Nor did we discover any pathological changes during our histological examinations of the organs either. There were no signs of irritating action of Tercuronium on the site of its administration (ear vein).

Moreover, in acute experiments on two rabbits (without anesthesia) and on two narcotized cats, we did not discover any effect of Tercuronium on the blood coagulation rate and resistance of the erythrocytes.

In order to study the allergizing action of Tercuronium, we used the Arthus-Sakharov phenomenon. Experiments were carried on three rabbits. Tercuronium was injected to each rabbit in a dose of 0.2 to 0.25 ml 0.02 mcM/kg subcutaneously on the left side of the back in a volume of 0.2 to 0.25 ml, and 1 ml of horse serum was injected into the right side of the back (also subcutaneously). We made seven injections at 5-day intervals. Horse serum alone was injected to the fourth (control) rabbit in the same order.

A marked allergic reaction was noted in all animals at the fifth or sixth stage of the experiment at the site of injection of horse serum: hyperemia, edema, punctate hemorrhage. There was no reaction at the site of repeated Tercuronium injections.

The results of the pharmacological studies of the proposed muscle relaxant Tercuronium, as compared with the known muscle relaxants, enable us to make the following conclusions.

1. In experiments on animals, the nervomuscular blocking activity of Tercuronium is 6 to 8 times higher than of d-tubocurarin and somewhat lower than of pancuronium.

2. In contrast to α-tubocurarin, Tercuronium given in a myoparalytic dose, does not produce histamine, does not block vegetative ganglia or affect the blood pressure and frequency of heart contractions. In experiments on cats, the blood pressure was only slightly reduced with a ten-fold dose of Tercuronium; the same reduction in the blood pressure can be attained with a myoparalytic dose of α-tubocurarin. Tercuronium given in a dose ten times exceeding the myoparalytic dose, does not affect the frequency of heart contraction. Pancuronium, as well as the proposed preparation Tercuronium, do not produce histamine or block vegetative ganglia. Due to an unknown reason pancuronium causes a stable rise in the arterial pressure, which results in increased hemorrhage in surgical operations and in accelerated pulse rate.

3. In conditions of artificial lung ventilation, cats and rabbits well tolerate administration of very large quantities of Tercuronium (10 to 20 mcM/kg of body weight which 200 times exceeds its myoparalytic dose). In the same conditions, a lethal drop of the arterial pressure is observed with α-tubocurarin given in a dose 5 to 10 times exceeding its myoparalytic dose.

4. The antagonistic (deblocking) effect of neostigmin (the main antagonist to nondepolarizing muscle relaxants) is stronger with Tercuronium than with pancuronium or α-tubocurarin. For example, in experiments of cats, neostigmin given in a 0.1 mg/kg intravenous injection, completely removed the blocking effect of five myoparalytic doses of Tercuronium within five minutes (against only three myoparalytic doses of α-tubocurarin and pancuronium).

In experiments on decerebrated cats we did not observe mutual strengthening of fluorothane and Tercuronium action on blood pressure while α-tubocurarin strengthened the negative action of fluorothane, and their combined action could therefore be considered dangerous due to the developement of cardiovasular collapse.

We tried Tercuronium as a muscle relaxant in surgical operations on the abdominal and thoracic organs in 150 patients. The operations were carried out in conditions of intubation narcosis and artificial lung ventilation. Ether, fluorothane, nitrous oxide and barbiturates were used as anesthetics.

In the first series of observations (120 operations) Tercuronium was used as the main muscle relaxant for maintaining relaxation of the muscles. Tracheal intubation was carried out with muscle relaxation induced by dithilin-group agents. On completion of the intubation, Tercuronium was injected in a dose of 0.12 − 0.15 mg/kg (1-2 ml of a 0.5 percent solution). No changes in arterial pressure ar frequency of heart contractions, that could be attributed to the injection of Tercuronium, were observed. Complete muscle relaxation with the absence of active respiration continued on an average of 40 minutes. If, with the first signs of restoration of the muscle tone, we made another intravenous injection of Tercuronium in a dose constituting ⅓ to ½ of the initial one, complete relaxation continued for further 60 – 90 minutes. Injection of proserpin at the end of an operation (2.5 mg) always resulted in quick (within a few minutes) restoration of active respiration in full volume. We did not observe any case of insufficient efficacy of proserpin, muscular atomia, or insufficiency of active respiration, or recurarization, in the postoperative period. The electromyographic analysis of the character of Tercuronium action on the nervomuscular conduction has proved that the preparation is a nondepolarizing muscle relaxant.

In the second series of observations (30 operations), Tercuronium was used for both maintaining muscle relaxation and intubation of the trachea. For this purpose, Tercuronium was used intravenously in a dose of 0.25 to 0.3 mg/kg. The muscles completely relaxed in 80 to 90 sec after the injection and provided unobstructed intubation. The action of this dose of Tercuronium was not accompanied by cardiovacular disorders or any other complications. The relaxation continued for about an hour. For a longer relaxation of muscles, a repeated injection of Tercuronium in a dose of 0.05 to 0.08 mg/kg was required. In this series of observations, the efficiency of proserpin as a deblocking agent was also complete and there were no cases of muscle atomia, respiratory insufficiency, or recurarization in the postoperative period.

Clinical observations have thus corroborated the results of the experiments and have also shown that Tercuronium is a nondepolarizing muscle relaxant free of the disadvantages inherent in the known relaxants α-tubocurarin, pyrolaxon and pancuronium. The proposed preparation tercuronium makes it possible to carry out safe and controlled relaxation of muscles as compared with the known pereparations α-tubocurarin, pyrolaxon and even pancuronium. Moreover, using Tercuronium for intubation of the trachea, makes it possible to do without preparations of the dithilin type, depolarizing relaxants possessing said disadvantages.

The active principle of Tercuronium, viz., p,p''-bis-triethylammonio-n-terphenyl dibenzenesulphonate having the structure

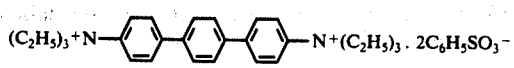

is a new compound that has not been described in literature. This is a white crystalline powder slightly green when exposed to air, melting at 228° to 229° C with decomposition. The powder is readily soluble in water; its aqueous solution is colourless, transparent, and stable in the presence of a stabilizer (3 ml of a 0.1 N HCl per liter of water). A 0.0012 percent solution of the active principle in a 0.01 N solution of hydrochloric acid has a specific absorption spectrum in the U-V region, with a maximum at 285 ± 2 nm and a minimum at 237 ± 1 nm.

The chemistry of the process for preparing the proposed compound is as follows:

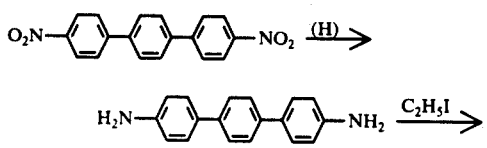

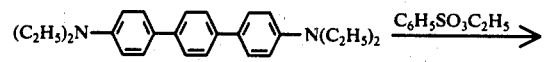

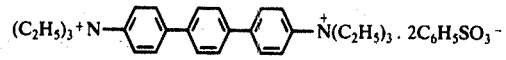

The method for preparing p,p''-bis-triethylammonio-n-terphenyl dibensenesulphonate consists in reduction of p,p'' p,p''-diamino-p-terphenyl, alkylation to n,n''-diamino-n-terphenyl, alkylation of p,p''-diamino-p-terphenyl to p,p''-bis-diethylamino-p-terphenyl with ethyl iodide and quaternization of n,n''-bis-diethylamino-p-terphenyl with ethyl ester of benzenesulphonic acid to p,p''-bis-triethylammonio-p-terphenyl benzenesulphonate.

The starting substance, p,p''-dinitro-p-terphenyl, is a known substance obtained by nitration of p-terphenyl with fuming nitric acid.

p,p''-Dinitro-p-terphenyl can be reduced, for example, by catalytic hydrogentation in an autoclave for 2 to 3 hours, or with stannous dichloride in concentrated hydrochloric acid in the course of three hours.

But a quicker process (with a quantitative yield) can be reduction of p,p''-dinitro-p-terphenyl to p,p''-diamino-p-terphenyl with hydrazine hydrate in the presence of Raney nickel in an inert organic solvent (e.g. ethylene glycol) with heating. The process continues for a few minutes.

Alkylation of p,p''-diamino-p-terphenyl can be done with various alkylating substances. For example, alkylation can readily be performed with ethyl iodine in the presence of an agent that binds iodine, in an inert organic solvent, with heating.

Quaternization of p,p''-bis-diethylamino-p-terphenyl is performed in a solution of ethyl ester of benzenesulphonic acid with heating.

The proposed method for preparing p,p''-bis-triethylammonio-p-terphenyl dibenzenesulphohate consists of three steps. The process requires little time and ensures good yields. The synthesis employs widely known reagents and solvents, and purification of the end product presents no difficulties. This method can be readily realized in industrial conditions and is commercially feasible.

For a better understanding of the invention, the following examples of its practical embodiment are given by way of illustration.

EXAMPLE 1

Preparation of p,p''-bis-triethylammonio-p-terphenyl dibenzenesulphonate.

a. Reduction of p,p''-dinitro-p-terphenyl

A 1-liter flask provided with a reflux condenser, a stirrer, a thermometer and a dropping funnel is loaded with 10 g of n,n''-dinitro-n-terphenyl in 500 ml of ethyleneglycol, and then 5 ml of freshly prepared Raney Ni are added. Next, the mixture is heated and stirred (the temperature inside the flask is 165° to 170° C) and 15 ml of a 99 percent solution of hydrazine hydrate are added in drops avoiding intense foaming.

The components are dissolved in a few minutes, then activated carbon is added. In 10 to 15 minutes the hot solution is filtered and the filtrate cooled. The precipitate is washed on the filter with alcohol, and dried.

The yield of p,p''-diamino-p-terphenyl is 8.1 g (quantitative yield). The product is creamy in colour; it does not require additional purification. The m.p. is 240° C (according to literature, 241° to 242° C).

b. Alkylation of p,p''-diamino-p-terphenyl

A 250-ml flask provided with a reflux condenser and a stirrer is loaded with 8 g of p,p''-diamino-p-terphenyl, 10 g of calcium carbonate, 100 ml of dimethylformamide, 10 ml of water and 23 ml of ethyl iodide. The mixture is heated on a bath at 120° to 130° C. The components are dissolved within a few minutes, and precipitation begins immediately. Heating is continued for two hours with active stirring, and the suspension is cooled.

The precipitate is separated on a filter and crystallized out of 100 ml of dimethyl formamide to isolate 7.65 g (70 percent) or p,p''-bis-diethylamino-p-terphenyl, a pale beige substance melting at 198° C.

Found, in percent: C 83.30, 83.42; H 8.68, 8.61; N 7.63, 7.61. $C_{26}H_{32}N_2$ Calculated, in percent: C 83.82; H 8.65; N 7.52 c. Quaternization of p,p''-bis-diethylamino-p-terphenyl

A 100-ml flask is loaded with 7.5 g of p,p''-bis-diethylamino-p-terphenyl and 20 ml of ethyl ester of benzenesulphonic acid, and the contents are heated for an hour on a Bath at a temperature of 140° C.

A solution is formed during the first thirty minutes, and by the end of heating a precipitate is crystallized out. The reaction mixture is cooled and processed with absolute ether with subsequent filtration.

The pale beige precipitate is crystallized out of 100 ml of acetone-water solution (10:1) with activated carbon. The yield of p,p''-bis-triethylammonio-p-terphenyl is 10 g (70 percent of theory). This is a white substance that becomes slightly green on exposture to air. It melts at 228° to 299° C with decompostion. The product is dried in vacuum and kept in the dark.

Found, in percent: C 67.97, 68.22, H 7.76, 7.66; N 3.80, 3.90; S 8.75, 8.55. $C_{42}H_{52}N_2O_6S_2$ Calculated, in percent: C 67.72, H 7.04, N 3.76, S 8.59

EXAMPLE 2

Preparation of the medicinal form of p,p''-bis-triethylammonio-p-terphenyl dibenzenesulphonate.

p,p''-bis-triethylammonio-p-terphenyl dibenzenesulphonate is used in medicine as a 0.5 percent aqueous solution, 5 mg of the active principle per intravenous injection.

The aqueous solution contains a stabilizing agent, viz, hydrochloric acid, taken in a quantity of 0.01 mg per injection.

One liter of the 0.5 percent solution of the substance is prepared by dissolving 5 g of the active principle in distilled water in a 1-liter measuring flask at 20 ° C. Distilled water should contain a stabilizing agent, namely 3 ml of a 0.1 N solution of HCl per liter of water. The solution is stirred, filtered, and filled into 1-ml ampoules made of neutral glass. The ampoules are sterilized with steam at a temperature of 100° C for thirty minutes. The pH of the solution after sterilization is 3.7 (determined potentiometrically).

The reaction of the preparation with potassium iodide and potassium thiocyanide can be used for the identification test. The above-named reagents form precipitates with the proposed preparation that dissolve on heating.

The test for identity can be done also by measuring the absorption spectrum in the U-V region. The absorption maximum should be at 285 ± 2 nm and the minimum at 237 ± 1 nm.

Quantitative determination of a 0.5 percent solution can be done by spectrophotometric method based on measuring optical density of the test solution.

The ampoules should be kept in the dark.

What is claimed is:

1. A nondepolarizing muscle relaxant composition containing as the active ingredient an effective amount of p,p''-bis-triethylammonio-p-terphenyl dibenzenesulphonate in a pharamaceutical carrier.

2. A nondepolarizing muscle relaxant composition according to claim 1, in which water is used as the pharamaceutical carrier.

3. A nondepolarizing muscle relaxant composition according to claim 1, in which the active ingredient is present in the quantity of 5 mg/ml.

4. A nondepolarizing muscle relaxant composition according to claim 1, in which hydrochloric acid is used as a stabilizing agent.

5. A nondepolarizing muscle relaxant composition according to claim 4, in which hydrochloric acid is present in the quantity of 0.01 mg/ml.

* * * * *